US00PP35968P3

(12) United States Plant Patent
Sanabria Aguilar et al.

(10) Patent No.: US PP35,968 P3
(45) Date of Patent: Jul. 9, 2024

(54) BLUEBERRY PLANT VARIETY NAMED 'BLUECSOL9'

(50) Latin Name: ***Vaccinium corymbosum* L.**
Varietal Denomination: BLUECSOL9

(71) Applicant: CAMPOSOL S.A., Lima (PE)

(72) Inventors: Kimberlayn Maria Apsara Sanabria Aguilar, Lima (PE); Milagros Janet Granda Mogollon De Montoya, Lima (PE); Luis Jose Montgomery Taboada, Lima (PE); Jorge David Romero Pajares, Lima (PE)

(73) Assignee: CAMPOSOL S.A., Lima (PE)

( * ) Notice: Subject to any disclaimer, the term of this patent is extended or adjusted under 35 U.S.C. 154(b) by 0 days.

(21) Appl. No.: 17/803,892

(22) Filed: Jan. 11, 2023

(65) Prior Publication Data

US 2023/0270028 P1 Aug. 24, 2023

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

*Primary Examiner* — Susan McCormick Ewoldt
(74) *Attorney, Agent, or Firm* — Ladas & Parry LLP

(57) ABSTRACT

A new and distinct evergreen blueberry variety with zero chill requirement named 'BLUECSOL9', characterized by the following combination of traits: medium to strong vigor, semi-upright growth habit, produces large sized fruit, strong bloom intensity, oblate fruit shaped, high sweetness and medium acidity, and very firm fruit. Latin name of the genus and species: *Vaccinium corymbosum* L.

6 Drawing Sheets

Latin name: *Vaccinium corymbosum* L.
Variety denomination: Blueberry plant named 'BLUECSOL9'.

CROSS REFERENCE TO RELATED APPLICATIONS

This application claims priority to a Peruvian Breeder's Rights Application No. 73-2022 filed on Jan. 14, 2022, the entire contents of which is incorporated by reference herein.

BACKGROUND OF THE INVENTION

The present invention relates to a new *Vaccinium corymbosum* L. plant, which was selected from open pollination between 'Biloxi' (*Vaccinium corymbosum* L., public plant) as the female (seed) parent and pollen from an unidentified variety (*Vaccinium corymbosum* L.). Berry seeds of plants of the 'Biloxi' variety were collected from different fields, located in Viru, La Libertad, Peru at the beginnings of 2016 to extract the seeds. 11805 seedlings at high density were planted under field conditions in December of the same year.

The seedlings were evaluated during 3 growing season (2017, 2018 and 2019). The breeding method used was phenotypic recurrent selection. In December 2019 one of the seedlings, 'BLUECSOL9', was isolated due to its good quality fruit, long postharvest life, and high yield potential. 'BLUECSOL9' was asexually propagated by softwood cuttings in a nursery, located in Viru, La Libertad, Peru. 5 rooted cuttings were planted in an experimental test plot, located in Viru, La Libertad, Peru with the aim to confirm the distinctness, and stability of the characteristics observed. From December 2020 until the present, said test plot has shown that the unique features of this new *Vaccinium* variety are stable and reproduce true to type in successive generations of asexual propagation. In addition, 'BLUECSOL9' was subsequently propagated by softwood cutting and tissue culture and an additional plot, with 100 plants were planted in December 2021 in the same location. This new plot has maintained up to the present the distinctness, and stability characteristics of the new variety of *Vaccinium corymbosum* L.

SUMMARY OF THE VARIETY

The following is a summary of the description of the new and distinct variety of blueberry 'BLUECSOL9' was selected in Viru, La Libertad, Peru in December 2019. 'BLUECSOL9' has not been observed under all environmental conditions. The phenotype may vary somewhat with variations in the environmental conditions such as temperature and light intensity, without, however, any variance in genotype. 'BLUECSOL9' is an evergreen blueberry variety with zero chill requirement. The following are the most distinguishing traits of this new variety: medium to strong plant vigor, semi-upright growth habit, ovate leaf shape, globose corolla shape, oblate fruit shaped, large sized fruit, strong bloom intensity, high sweetness and medium acidity and very firm fruit.

'BLUECSOL9' was selected as an early variety, with high yield potential, excellent fruit quality and post-harvest life.

BRIEF DESCRIPTION OF THE DRAWINGS

The accompanying color photographs show typical bush, leaves, flower, and fruit characteristics of the new *Vaccinium corymbosum* L. 'BLUECSOL9'. Colors shown are as accurate as can be reasonably reproduced by the photographic means. Photographs were taken of 2 and 4-year-old plants grown in fields, located in Viru, La Libertad, Peru.

DETAILED BOTANICAL DESCRIPTION

Figure 1:
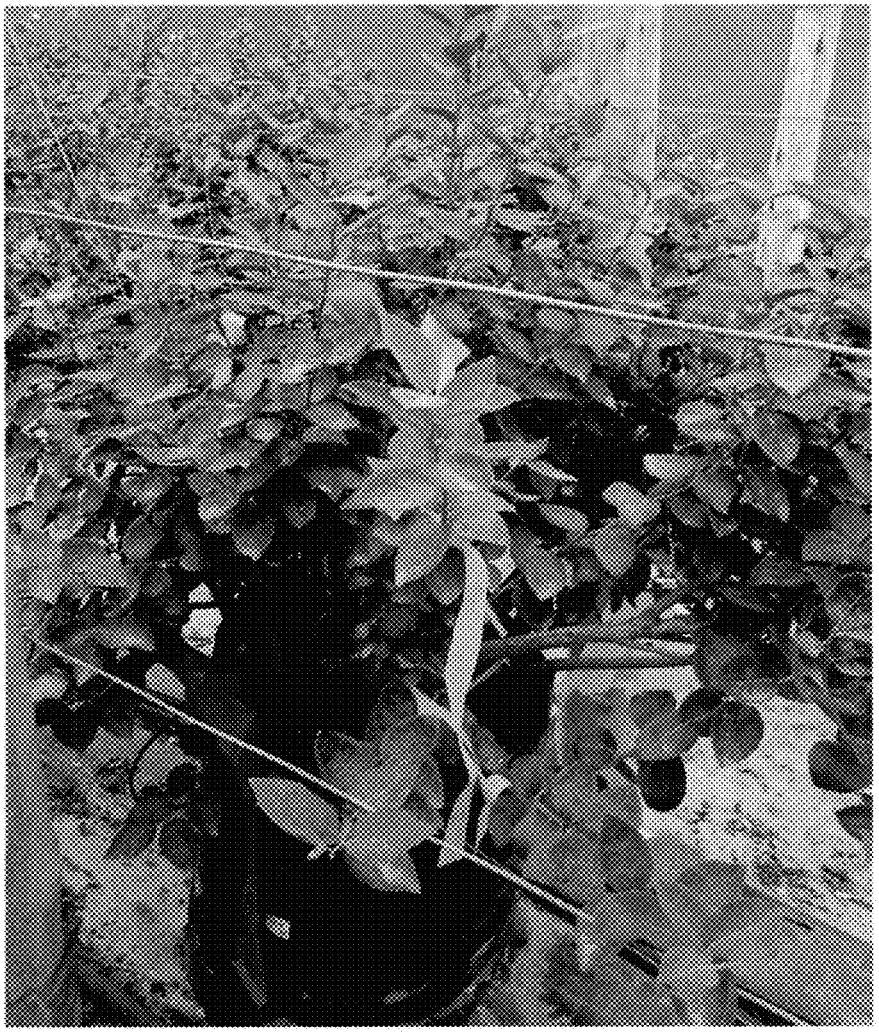
FIG. 1.—Shows typical bush with semi-upright growth habit on 4-year-old plant of the new variety 'BLUECSOL9'.
Figure 2:
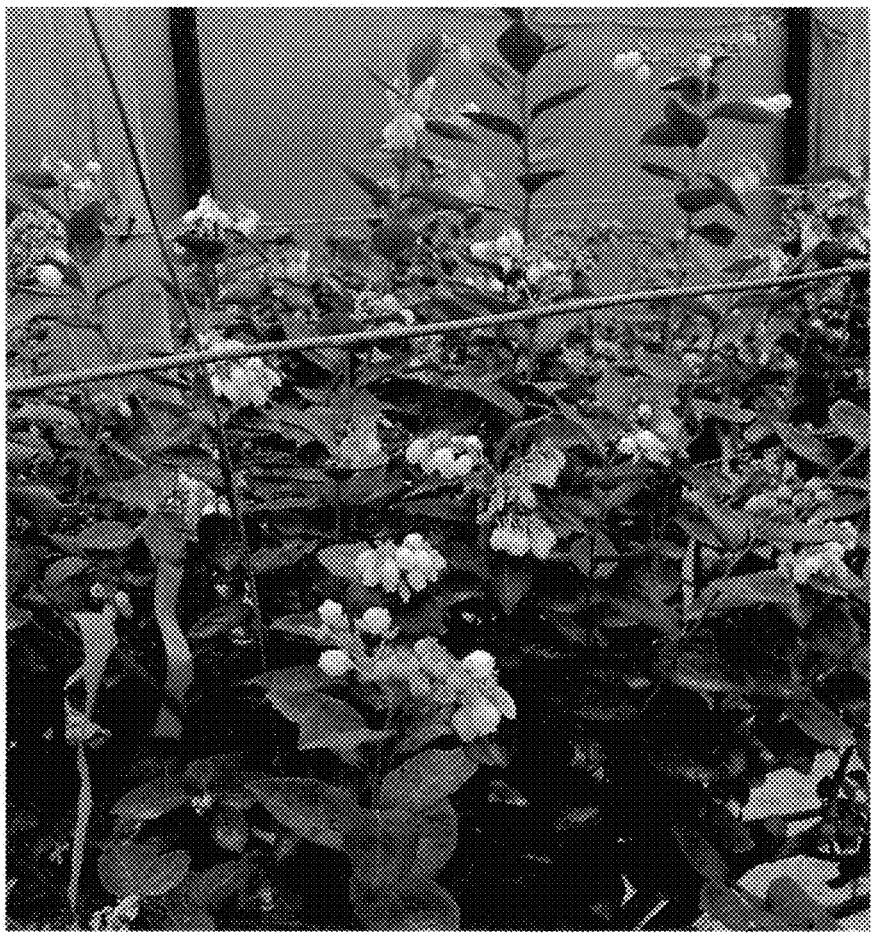
FIG. 2.—Shows several clusters of opening flowers on 4-year-old plant of the new variety 'BLUECSOL9'.
Figure 3:
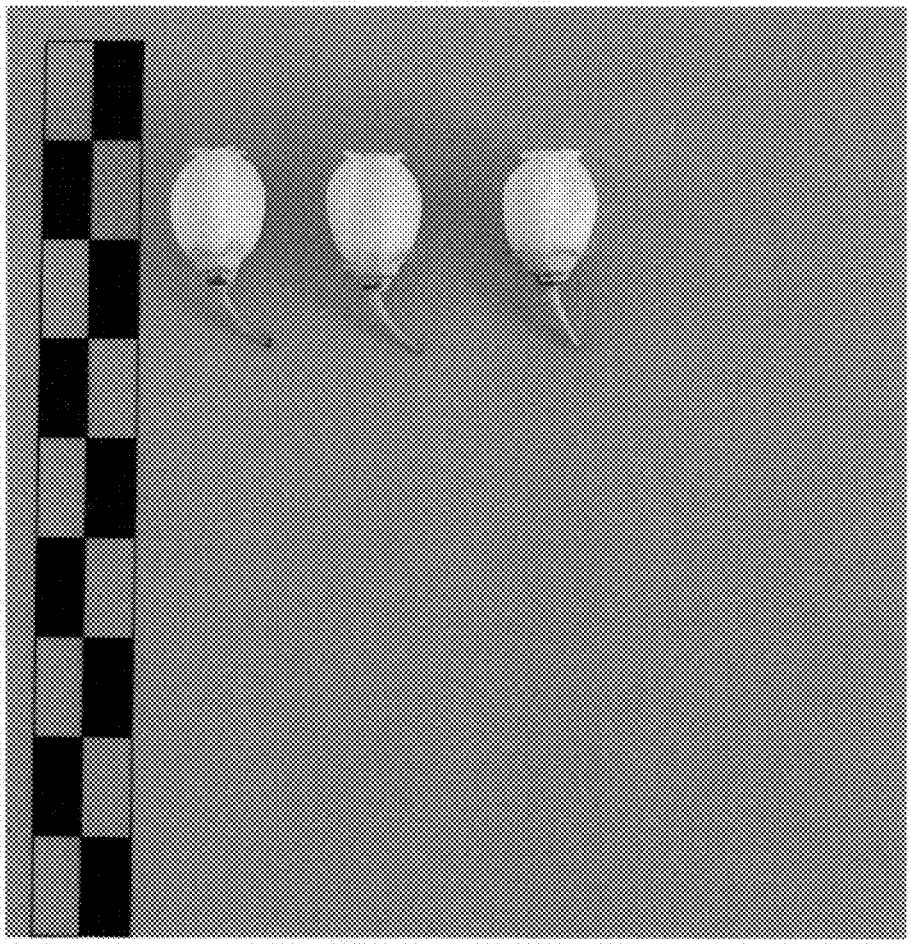
FIG. 3.—Shows the size and shape of the flower corolla on 2-year-old plant of the new variety 'BLUECSOL9'.
Figure 4:
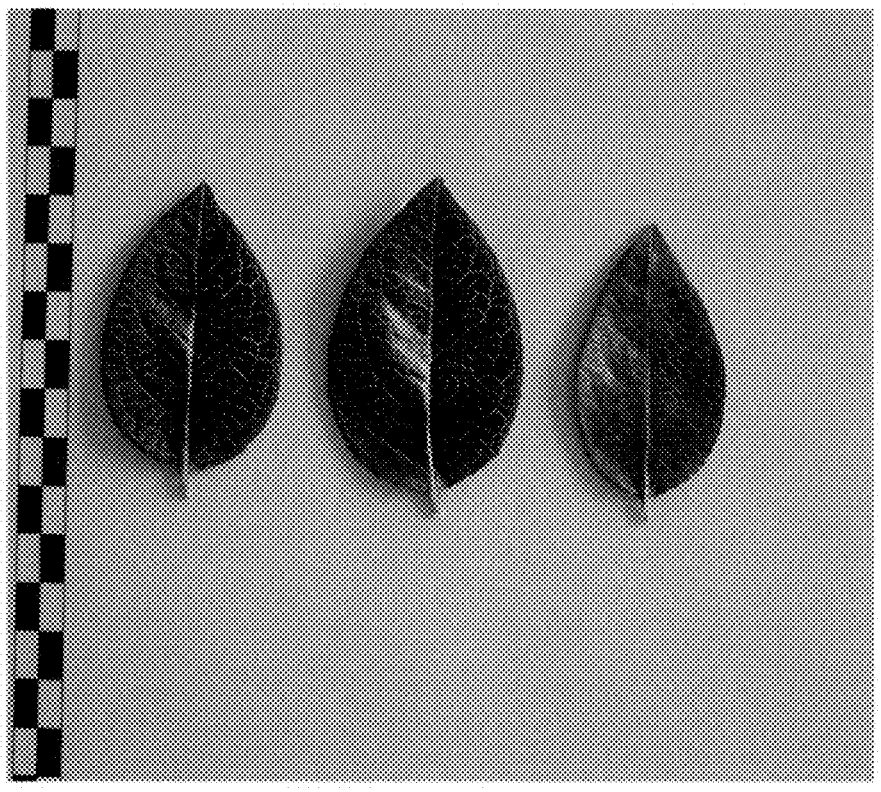
FIG. 4.—Shows the upper sides and shape of complete leaves on 2-year-old plant of the new variety 'BLUECSOL9'.
Figure 5:
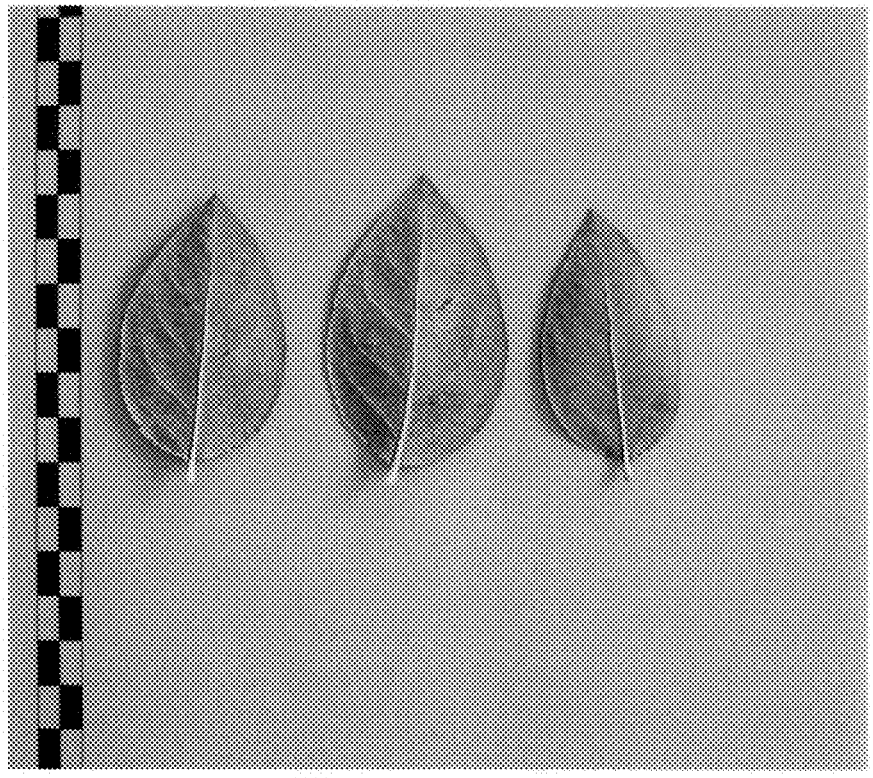
FIG. 5.—Shows the underside of a complete leave on 2-year-old plant of the new variety 'BLUECSOL9'.
Figure 6:
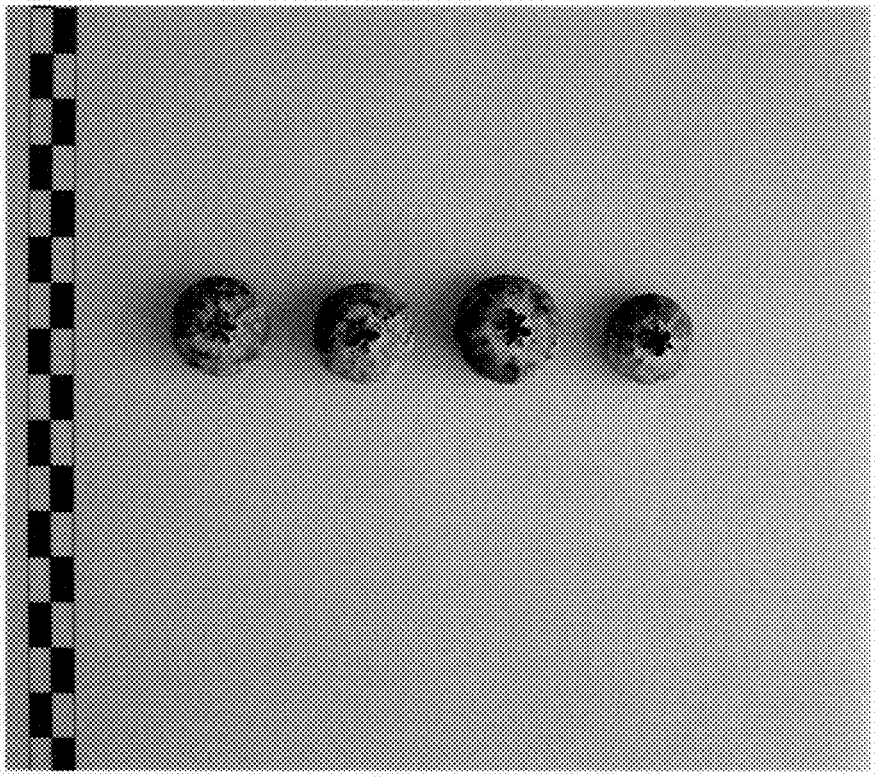
FIG. 6.—Shows the size and shape of the fruits on 2-year-old plant of the new variety 'BLUECSOL9'.

The following botanical description detailed forth distinctive traits of 'BLUECSOL9'. The data were collected from clones established in an experimental test plot in Peru on 2-year-old plants. Color descriptions are based on the Munsell® Plant Tissue Color Book scale of 2012 and Pantone® color codes of 2023.

Classification:
- *Family*.—Ericaceae.
- *Species*.—*Vaccinium corymbosum* L.
- *Common name*.—Southern Highbush Blueberry.
- *Cultivar name*.—'BLUECSOL9'.

Parentage:
- *Female parent*.—'Biloxi' (Unpatented).
- *Male parent*.—Unidentified variety.

Plant:
- *Vigor*.—Medium to strong.
- *Growth habit*.—Semi-upright.
- *Height*.—Mean of 150 cm.
- *Width*.—Mean of 130 cm.
- *Internode length*.—Mean of 21.56 mm.
- *Evergreenness*.—Evergreen.
- *Chilling requirements*.—0 hours below 7° C.
- *Ease of propagation*.—'BLUECSOL9' shows a high-rate multiplication when it was propagated by tissue culture.
- *Color of 1-year-old rough bark observed November 8*.—Brown Munsell® 5GY 6/4.

Leaves:
- *Leaf arrangement*.—Alternate.
- *Length*.—Mean of 55 mm.
- *Width*.—Mean of 35 mm.
- *Length/width ratio*.—1.57.
- *Surface texture in the upper*.—Smooth and shiny.
- *Surface texture in the lower*.—Smooth.
- *Shape*.—Ovate.
- *Shape of the apex*.—Obtuse.
- *Shape of the base*.—Obtuse.
- *Venation pattern*.—Pinnate and brochidodromous.
- *Margin*.—Serrate.
- *Color on upper side of old leaves*.—Green Munsell® 5GY 3/4.
- *Color on upper side of young leaves*.—Green Munsell® 5GY 4/6.

Petiole:
- *Length*.—Mean of 4.4 mm.
- *Diameter*.—Mean of 2 mm.
- *Color*.—Green Munsell® 5GY 7/6.

Flowers:
- *Flower cluster*.—Medium.
- *Flower fragrance*.—Little or none.
- *Inflorescence length*.—Mean of 42 mm.
- *Size of corolla tube*.—Mean of 12 mm (from pedicel attachment point to corolla tip excluding the pedicel).
- *Corolla shape*.—Globose.
- *Length of corolla tube*.—Mean of 12.3 mm.
- *Corolla tube color*.—White Pantone® 11-0601 TPX.
- *Time of beginning flowering on a one-year-old shoot*.—Early.
- *Time of beginning of flowering on the current season's shoot*.—Early.

Stamen:
- *Length*.—Mean of 0.7 cm.
- *Number per flower*.—About 10 to 11.
- *Color of filament*.—Green Munsell® 2.5GY 8/4.
- *Color of anther*.—Yellow Munsell® 7.5YR 7/10.

Pistil:
- *Number per flower*.—1.
- *Style color*.—Green Munsell® 2.5GY 7/10.
- *Style length*.—Top of ovary to stigma tip. 8 mm.

Fruits:
- *Diameter of calyx aperture on mature berry*.—Mean of 4.5 mm.
- *Diameter of depth of calyx on mature berry*.—Mean of 2.7 mm.
- *Detachment force for ripe berries* (*easy, medium, hard*) .—Easy.
- *Berries per cluster*.—About 8 to 12.
- *Width*..—About 16 to 20 mm.
- *Weight*.—Mean of 2.5 g per berry.
- *Shape*.—Oblate.
- *Intensity of fruit bloom*.—Strong.
- *Pedicel scar*.—Mean of 2 mm.
- *Color of unripe fruit*.—Light green Munsell® 2.5GY 6/8.
- *Color of fruit flesh*.—Munsell® 2.5GY 7/4.
- *Color of mature fruit skin with bloom*.—Dapple gray Pantone® 16-3907 TCX.
- *Color of mature fruit skin without bloom*.—Dark navy Pantone® 19-4013 TCX.
- *Fruit firmness*.—Very firm.
- *Fruit acidity*.—Medium.
- *Fruit sweetness*.—High.
- *Market use of fruit*.—Fresh market.

Seeds:
- *Color*.—Brown Munsell® 7.5YR 4/4.
- *Seeds per berry*.—Mean of 10 seeds.

Reproductive organs:
- *Pollen abundance*.—Abundant.
- *Self-compatibility*.—High degree of self-compatibility.
- *Disease, insects, and mites*.—No sensitivity to any disease and pest has been observed for 'BLUECSOL9'.

'BLUECSOL9' has high productive potential. The harvest begins after 6 months of the planting or pruning of the plants on the field and lasts for 24 weeks. Plant productivity in the first season is about 2.5 to 3.5 kg per plant and in the second season is around 3.5 to 4.0 kg per plant. 80% of the harvest is concentrated in 14 weeks.

Storage qualities: 'BLUECSOL9' has a shelf life of more than 49 days under modified atmosphere storage at 1° C. and 35 days under controlled atmosphere storage at 1° C.

Plant hardiness zone: The plants of the 'BLUECSOL9' variety were tested under the arid conditions of the northern coast of Peru, where the maximum temperatures in the year are 32° C. and the minimum are 13° C. The 'BLUECSOL9' variety can produce fruit all year round and does not require temperatures below 7° C. for flower induction. The area where its behavior was observed and evaluated does not have extreme temperatures to be able to determine cold or heat resistance.

COMPARISON TO CLOSEST VARIETY

'BLUECSOL9' is distinguished from 'Biloxi' variety in the following characteristics:

Color on upper side of old leaves in plants of 'Biloxi' (Unpatented) variety is green Munsell® 2.5G 3/2, whereas the color on upper side in leaves of 'BLUECSOL9' is green Munsell® 5GY 3/4.

The length of the inflorescence in 'Biloxi' (Unpatented) is medium and in 'BLUECSOL9' is short.

Fruit size of 'Biloxi' (Unpatented) is medium and shows high acidity, whereas in 'BLUECSOL9' fruit size large fruits and medium acidity.

The diameter of depth of calyx on mature berry in 'Biloxi' (Unpatented) is shorter than 'BLUECSOL9'.

Intensity of fruit bloom in in 'Biloxi' (Unpatented) is weaker than 'BLUECSOL9'.

COMPARISON TO COMMERCIAL VARIETY

'BLUECSOL9' is distinguished from 'Emerald' (U.S. Plant Pat. No. 12,165) in the following characteristics:

The vigor of 'BLUECSOL9' is greater than 'Emerald' (U.S. Plant Pat. No. 12,165).

The color of 1-year-old shoot in 'Emerald' is green Munsell® 2.5GY 6/6, whereas in 'BLUECSOL9' is green Munsell® 2.5GY 6/4.

The abundance of pollen in 'Emerald' (U.S. Plant Pat. No. 12,165) is very high, whereas in 'BLUECSOL9' is high.

Fruit size in 'Emerald' (U.S. Plant Pat. No. 12,165) is medium, whereas in 'BLUECSOL9' is large.

The depth of the calyx basin on mature berry in 'Emerald' (U.S. Plant Pat. No. 12,165) is greater than in 'BLUECSOL9'.

Fruit firmness in 'BLUECSOL9' is greater than 'Emerald' (U.S. Plant Pat. No. 12,165).

Intensity of bloom in 'Emerald' (U.S. Plant Pat. No. 12,165) is medium, whereas in 'BLUECSOL9' is strong.

What is claimed is:

1. A new and distinct blueberry plant named 'BLUECSOL9' substantially as illustrated and described.

* * * * *